United States Patent [19]
Madden et al.

[11] Patent Number: 5,170,925
[45] Date of Patent: Dec. 15, 1992

[54] LAPAROSCOPIC STAPLER WITH KNIFE MEANS

[75] Inventors: Martin Madden, Cincinnati; Mark Ortiz, Milford, both of Ohio

[73] Assignee: Ethicon, Inc., Somerville, N.J.

[21] Appl. No.: 671,059

[22] Filed: Mar. 18, 1991

[51] Int. Cl.$^5$ .................................................. A61B 17/072
[52] U.S. Cl. ..................................... 227/175; 227/180; 227/19
[58] Field of Search ............... 227/175, 176, 177, 135, 227/120, 19, 144, 152, 180; 606/139, 213, 142

[56] References Cited

U.S. PATENT DOCUMENTS

| | | | |
|---|---|---|---|
| 3,593,903 | 7/1971 | Astafiev et al. | 227/19 |
| 4,169,476 | 10/1979 | Hiltebrandt | 606/142 |
| 4,520,817 | 6/1985 | Green | 227/19 |
| 4,633,874 | 1/1987 | Chow et al. | 227/19 |
| 4,784,137 | 11/1988 | Kulik et al. | 227/177 |
| 5,040,715 | 8/1991 | Green et al. | 227/176 |

FOREIGN PATENT DOCUMENTS

| | | | |
|---|---|---|---|
| 399701 | 10/1990 | European Pat. Off. | |
| 2437820 | 6/1980 | France | 606/142 |
| 728848 | 4/1980 | U.S.S.R. | |

Primary Examiner—Frank T. Yost
Assistant Examiner—Allan M. Schrock
Attorney, Agent, or Firm—Paul A. Coletti

[57] ABSTRACT

A four-row laparoscopic surgical staper cutting mechanism is described wherein stapling and cutting are remotely accomplished. Further, there is disclosed closure means which enable closure and stapling of the apparatus. Finally, such closure can take place either using lever or collar type means. This stapling apparatus is useful in performing surgical stapling functions through the cannula of a surgical trocar.

14 Claims, 4 Drawing Sheets

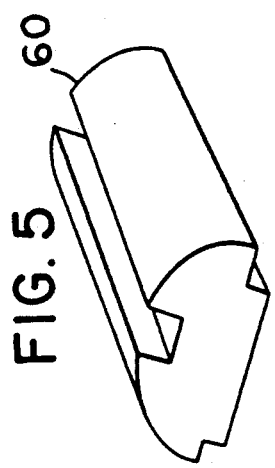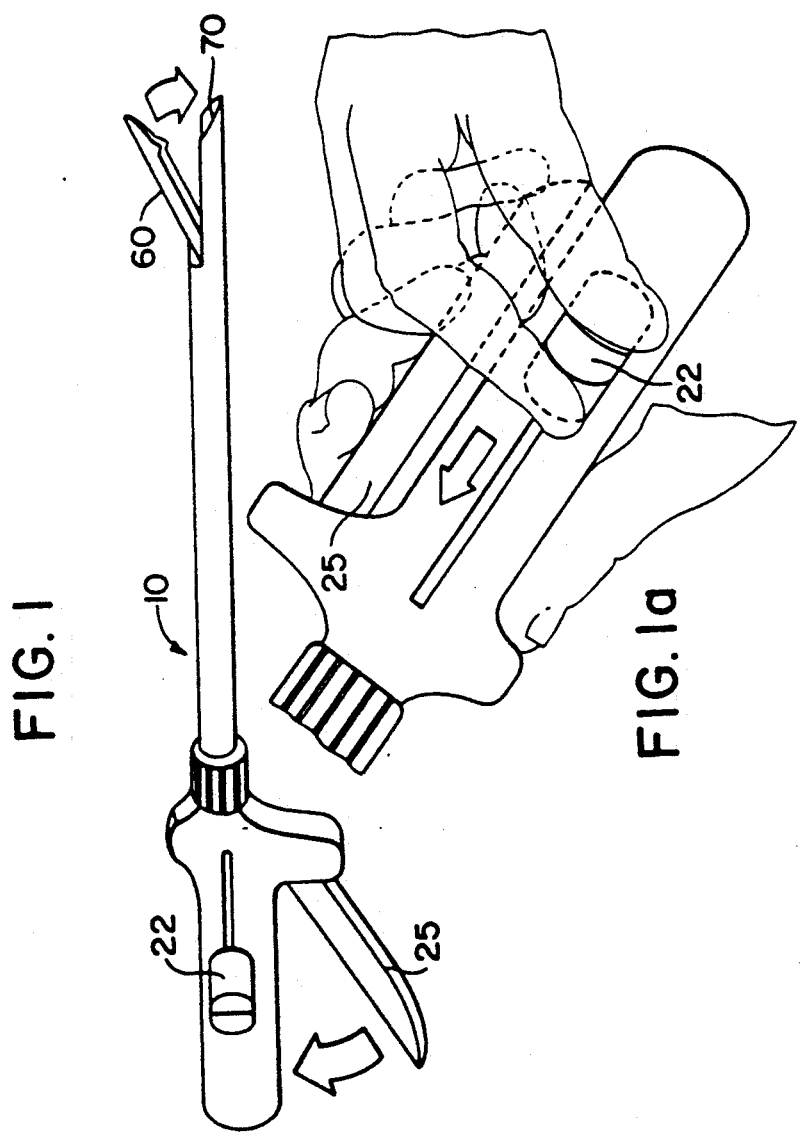

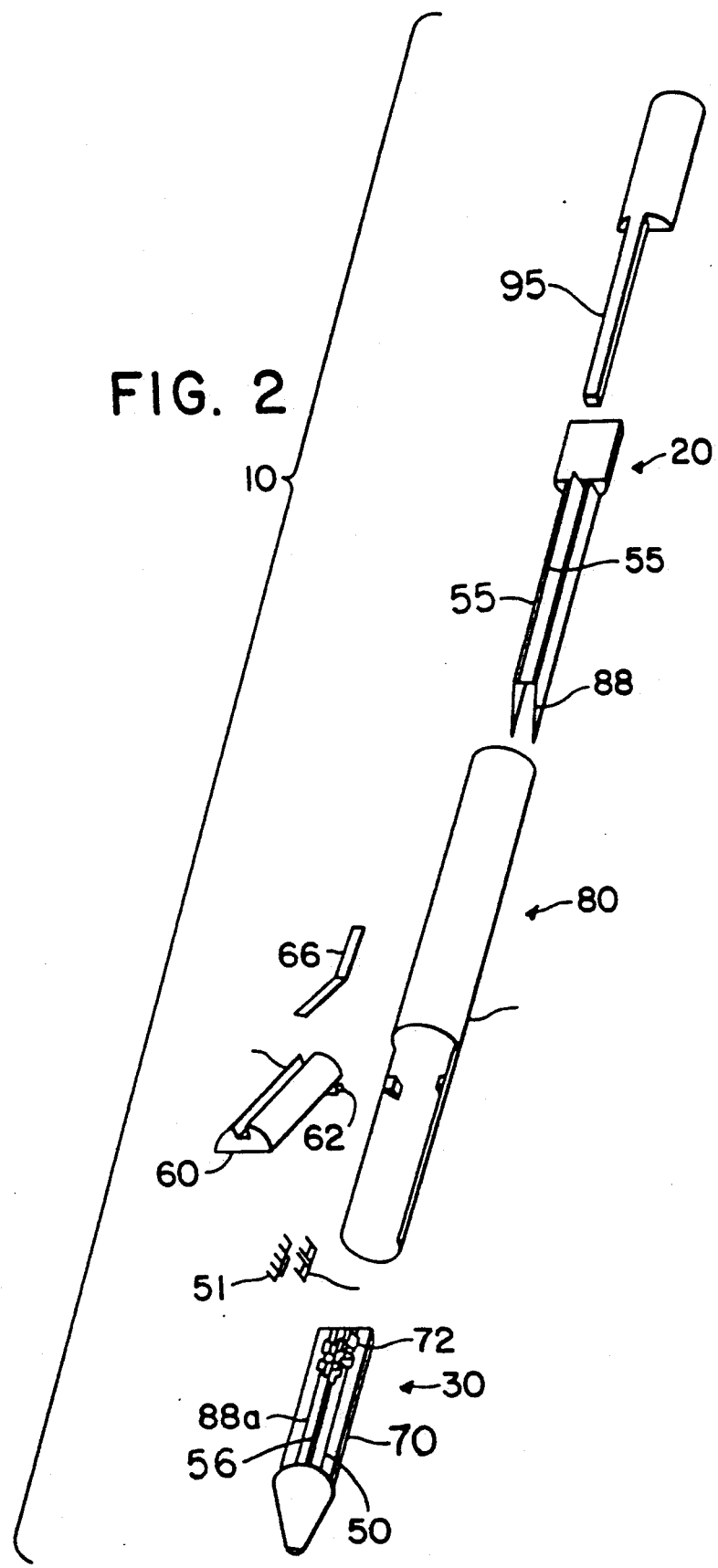

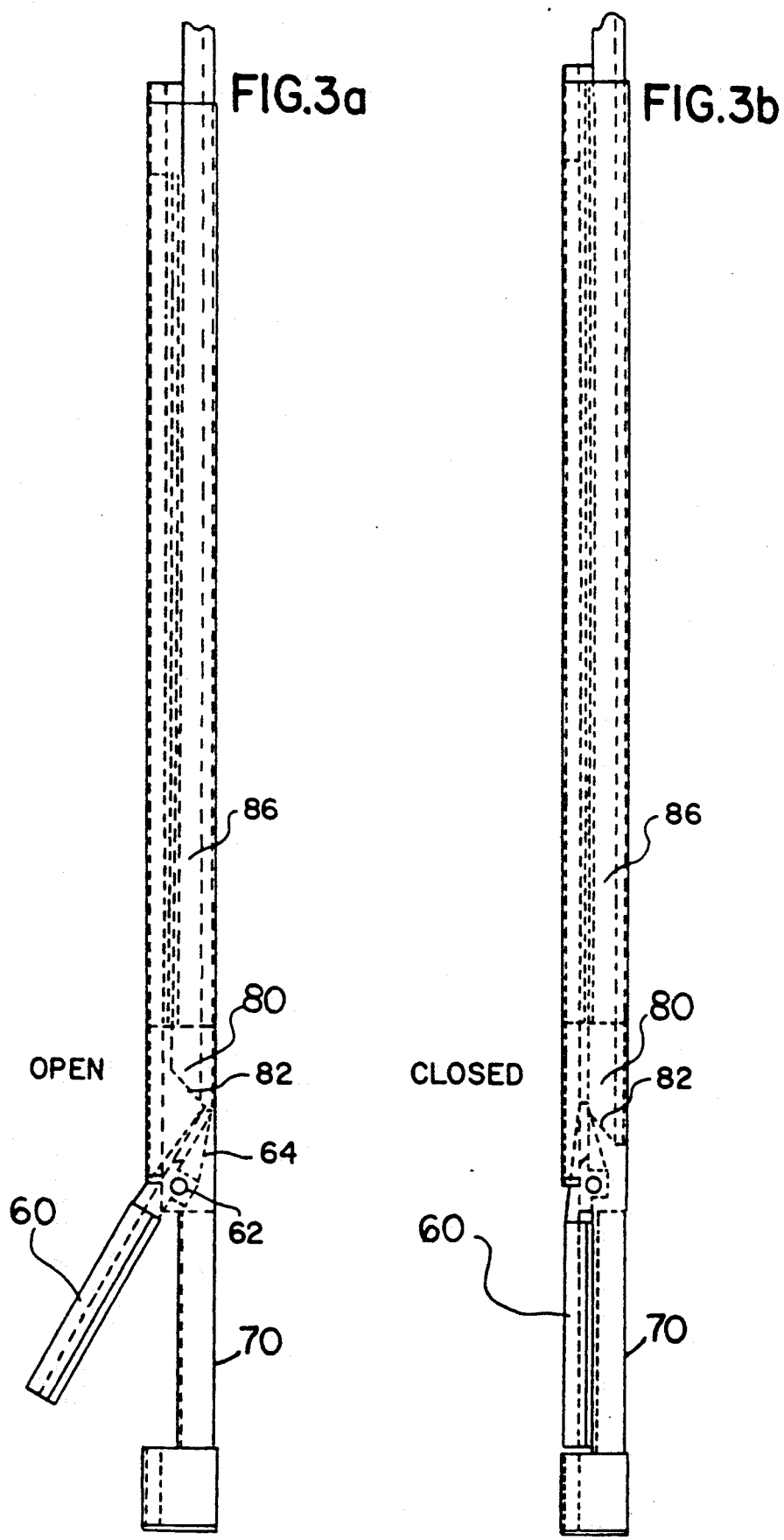

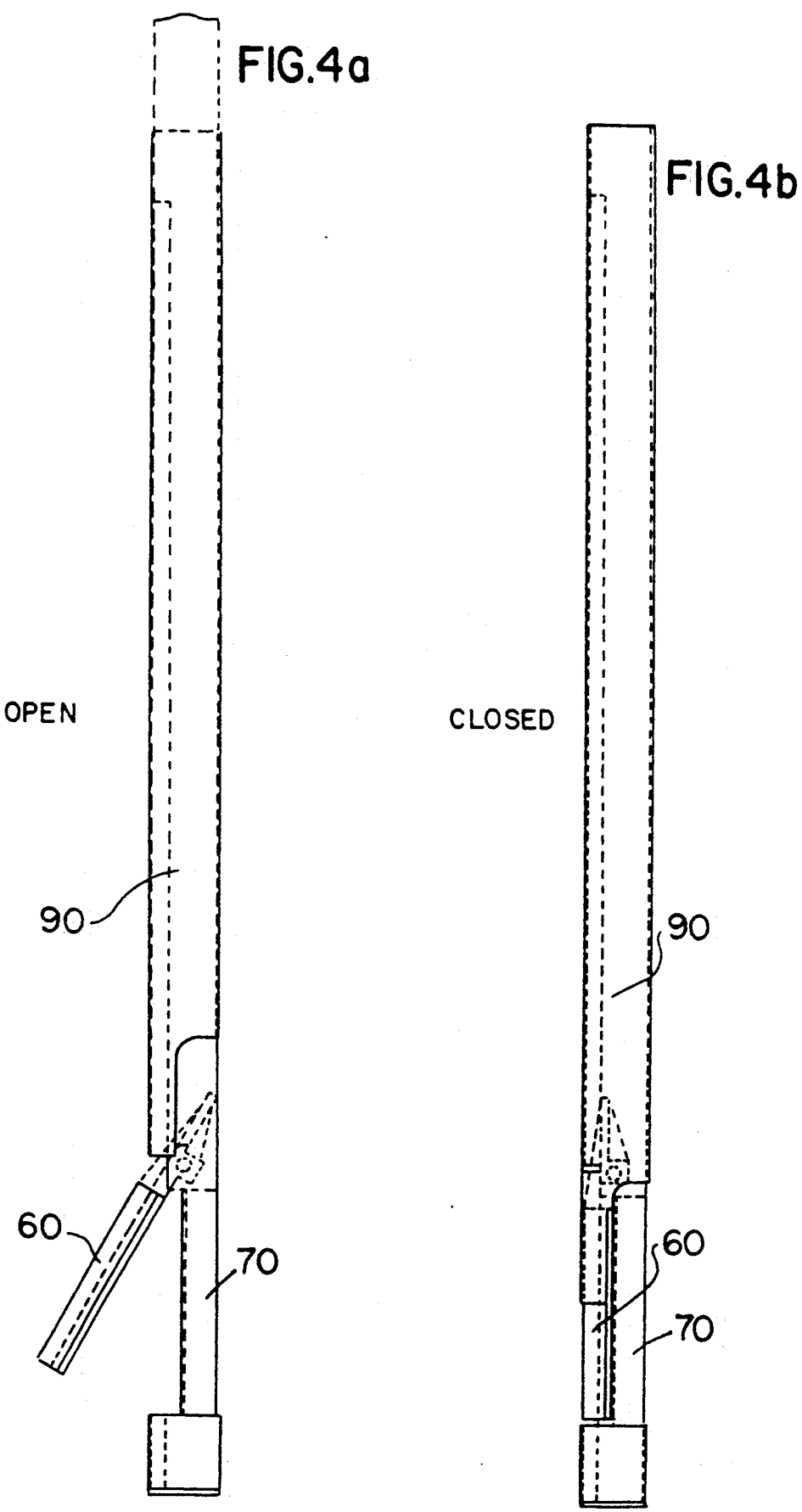

LAPAROSCOPIC STAPLER WITH KNIFE MEANS

FIELD OF THE INVENTION

Generally, this invention relates to surgical staplers. More specifically, it relates to surgical staplers useful with surgical trocars. Most specifically, this invention relates to laparoscopic surgical staplers which also contain cutting mechanisms useful within an insertion cannula and placed in the body through means of a surgical trocar.

BACKGROUND OF THE INVENTION

In the late 1980's, the use of surgical trocars has proliferated. Trocars are puncturing devices which allow the user access to the body cavity through a relatively small circular hole. These trocars generally have a diameter of about 3 mm to about 15 mm. They are capable of puncturing the abdominal wall and passing within the body cavity. When passing into the cavity, the trocar introduces an operating cannula contained around and along a sharpened obturator tip. The obturator usually has a circular cross-section. Upon insertion of obturator and cannula into the body cavity, the obturator tip may be removed, and the cannula remains in the body cavity. By passing surgical instruments and other devices or medications into the body via the surgical trocar cannula, surgical procedures are able to take place. Thus, it can be seen that much less tissue trauma results during the use of such trocars.

To this point only the most rudimentary surgical procedures have taken place using surgical trocars. One of the more important reasons for this lack of advancement is the incompatability of current surgical staplers and present surgical trocars. Current staplers are normally far too large for use within the body cavity except in the instance of full open surgery. Heretofore, it has been difficult to configure a surgical stapler that is capable of passing through the trocar cannula and yet also capable of stapling tissue within the cavity.

Further, it has not been possible to create a stapler wherein closure takes place and staples are fired and tissue is cut. In certain instances, it may be desirable to have this happen within the same stroke of a firing mechanism.

Also, because such laparoscopic staplers must carry only a few staples due to the shortened length of the stapler cartridge, it has been found that making such staplers with reloadable cartridges, or replaceable cartridges, has also been impossible.

Furthermore, when such devices are used, it is mandatory that certain functional characteristics of surgical staples still be provided. For instance, there still must be enough support within a driving and anvil-type mechanism so that staples are securely applied and tissue healing occurs.

Without arming the surgeon with one of the more important products for usage in surgical procedures, that is, the surgical stapler, it has been difficult to accomplish other than the most basic laparoscopic procedures. It has also limited the other possibilities in which one is able to provide such instruments to surgeons, which potentially would result in less tissue or other physical trauma to the patient.

SUMMARY OF THE INVENTION

It is an object of the invention to provide a surgical stapler configured to fit within a hollow cannula.

It is further an object of the invention to provide a surgical stapling instrument in which the anvil and firing mechanism of the instrument can compactly be transported and brought into close proximity with each other.

It is yet another object of the invention to provide a surgical stapling mechanism which provides for remote actuation by the user while the mechanism is placed within a laparoscopic cannula.

It is yet another object of the invention to provide a closure means for bringing together an anvil portion and a stapling portion of a surgical stapling mechanism.

Finally, it is an object of the invention to provide a surgical stapling mechanism which is protected by a tubular sheath for passage through a surgical trocar.

These and other objects of the invention are accomplished in a surgical stapling mechanism comprising a hollow tubular sheath with two open ends. At one of the open ends there is positioned an actuating mechanism. This actuating mechanism is connected through the hollow tubular sheath to a stapling mechanism. The tubular sheath and surgical stapling mechanism are capable of fitting through the hollow cannula.

The stapling mechanism comprises a firing portion and an anvil portion which is brought together by a closure means. The anvil portion and stapling portion are pivotable about one another so that the closure means can operate to bring the anvil and firing portion within close proximity for firing staples. Alternately, closure may be affected by having the cartridge pivot about the anvil, into proximity of the anvil.

Thus, in usage, the user is capable of placing the surgical stapler of this invention into a surgical trocar. The user then opens the anvil portion (with respect to the firing portion) so that tissue may be placed between the anvil and firing portions. The anvil is pivoted with respect to the firing or stapling portion so that tissue may be grasped by the stapler. In some instances there may be a knife put in place within the stapler so that cutting may also be done.

Actuation takes place remotely so that stapling can be accomplished within the stapling mechanism between the anvil and firing portions. After the staples are fired, the anvil is pivoted away from the firing mechanism so that tissue may be freed. Then, the entire stapling mechanism is passed out of the trocar so that a surgical procedure may be continued.

These and other objects of the invention may more readily be seen in the accompanying Detailed Description of the Drawings taken in combination with the Detailed Description of the Invention.

DETAILED DESCRIPTION OF THE DRAWINGS

FIGS. 1 and 1a are perspective views of a surgical stapler of the invention;

FIG. 2 is an assembly view of a surgical stapler of the invention;

FIGS. 3a and 3b are side views of the anvil closure mechanism of the invention;

FIGS. 4a and 4b are are plan views of an alternate anvil closure concept of the invention; and FIG. 5 is a perspective view of an anvil of the present invention.

DETAILED DESCRIPTION OF THE INVENTION

As can be seen the FIGS. 1-5, there is disclosed a surgical stapler 10 useful for laparoscopic applications. This stapler 10 has an actuating means 20 which may generally be connected to a remote trigger-type mechanism 25 at one end and connected to a firing mechanism 30 at its opposite end. This connection is made within a tubular sheath 80, as seen in FIG. 2. Sheath 40 holding the firing mechanism 30 as well as the actuating mechanism 20 is able to fit through a typical laparoscopic cannula. One of the more typical cannulas is described in Yoon, U.S. Pat. No. 4,535,773.

The surgical stapler of the present invention is one of the type which is capable of laying two double parallel rows 50 of staples 51. Optionally, there is a knife 55 which is disposed between the parallel rows 50 of staples 51. A typical surgical stapler with a configuration and a firing means as described in the present invention is described in Chow et al., U.S. Pat. No. 4,633,861 and Chow et al., U.S. Pat. No. 4,633,874, assigned to a common assignee, and herein also incorporated by reference.

The stapling mechanism as presently described can be remotely operated and is capable of being placed down a hollow cannula. Remote operation is possible due to the unique operating system which is described by the invention. First, as can be seen in FIGS. 1 and 2, the anvil 60 is pivotable about a staple holding cartridge 70. Alternately, the anvil 60 may be stationary, and cartridge 70 may pivot about anvil 60 in the same ways as described herein. This staple holding cartridge 70 typically holds four double parallel rows 50 of seven staples 51 each with a passageway 56 for knife blade 55 disposed down the middle. The anvil 60 is capable of pivoting toward and away from the staple holding cartridge 70 at pivot 62. The anvil pivots around pivot 62 on shaft 80.

In general overview as seen in FIGS. 2, 3a and 3b, anvil 60 is remotely actuated by means of an internal ramp 82 connected to both anvil 60 and to the actuating mechanism 20. With trigger 25 in the unforced or "open" position, internal ramp 86 containing cam surface 82 is out of contact with anvil 60 so that it pivots about the pivot point 62 on the shaft 80 and away from the staple holding cartridge 70. In such situations where there is no force applied to the lever 22, a return spring 66 pivots anvil 60 away from the staple holding cartridge 70. Squeezing trigger 25 causes ramp 82 to contact ramp 64 and overcome spring 66. Thus, when activated, anvil 60 lays either against the staple holding cartridge 70 or more preferably causes tissue to be entrapped between the anvil 60 and staple holding cartridge 70.

Of course, closure may take place in an alternate fashion by sliding an external collar (activated by trigger 25) over anvil 60, to cause anvil 60 to pivot against cartridge 70. Of course, opening the collar allows spring 66 to open anvil 60 away from cartridge 70. This will be later explained in detail.

More particularly, there is disclosed in this invention a method and system whereby the anvil 60 is forced to be firmly closed with tissue held between it and the staple cartridge 70. One of the basic methods of closure is seen in FIGS. 3a and 3b. There, it can be seen that the underside of the anvil 60 contains a sliding ramp or cam follower 64. This ramp 64 interacts with the cam surface 82 attached to internal ramp 86 or other similar types of devices which form the mechanism to close anvil 60 on cartridge 70. Then, a separate actuating mechanism comprising lever 22 as in FIGS. 1 and 1a, is forced forward to cause wedges 88 seen in the forward portion of FIG. 2, to contact drivers 72. The lever 22 and firing wedges 88 are formed from a singular one-piece metal strip. It is held in place in a narrow channel 88a. Operation is similar to that of typical surgical staplers, such that the drivers 72 drive staples 51 against anvil 60.

Because the anvil 60 is pivotable about pivot point 62 on the shaft 80, when the actuating mechanism trigger 25 forces the ramp 64 away from the underside (staple cartridge 70 side) of the sheath 80, the anvil 62 pivots and entraps tissue between the anvil 60 and staple carrying cartridge 70. Then the actuating mechanism lever 22 is forced further away from the shaft 80, that is toward the proximal portion of the staple carrying cartridge 70; wedges 88 come into contact with staple drivers 72 and act as firing wedges, much like the firing wedges used on typical surgical stapling devices as found in the Chow patents earlier incorporated by reference.

These out-of-phase wedges 88 are advanced out of line of the drivers 72, each of which fire two staples 51 at a time. The wedges 88 advance from distal to proximal end of the staple line. Alternately of course, the wedges 72 may be pulled from the proximal to the distal end of the staple line; however this is a less preferable method.

In much the same way the knife 55 held between the double Parallel rows of staples 50 may be pulled or pushed across the fired staple line with the surgical staples 51 emplaced in tissue, as previously described. A line of staples 50 may be placed down and then the anvil 60 is opened to release the tissue, and then allowed to close for retraction of stapler 10 including spent cartridge 70 and closed anvil 60 from the body. The spent staple cartridge 70 may be removed and replaced with another cartridge of similar size.

There is disclosed in FIGS. 4a and 4b a collar closure mechanism 90 which forces the anvil 60 shut. As seen in FIG. 4a, the anvil 60 can be actuated forward by squeezing trigger 25, much as in FIGS. 3a and 3b. Thereafter, the tissue is allowed to become entrapped between the anvil 60 and the staple carrying cartridge 70. The tissue is trapped by the collar 90 from the sheath 80, which is placed down and over the anvil 60 and the staple carrying cartridge 70, by use of the trigger 25 or other known actuation means connected to the actuating mechanism. This collar 90, therefore, keeps the anvil 60 locked against the staple carrying cartridge 70, and provides a strong reactive force for enabling the staples 51 to be fired against the anvil 60. Of course, return spring 66 overcomes the force of the anvil 60 when collar 90 is not in place over the anvil 60.

In much the same way as in FIGS. 3a and 3b, the firing wedges 88 from the lever 22 cause the staples 51 to be ejected from the staple carrying cartridge 70 and into the anvil 60 held with the collar 90 wrapped around it. After stapling and/or cutting have been completed, the collar 90 is retracted away from the anvil 60 so that return spring 66 can be used to pivot the anvil 60 around pivot point 62 and therefore loosen the tissue between the anvil 60 and the staple carrying cartridge 70. Thereafter, the anvil 60 can again be closed onto the staple carrying cartridge 70 with tissue placed between them, or retracted so that the entire stapling mechanism 10 may be drawn up the trocar cannula.

The operation with cutting and stapling can be accomplished as follows. First, after making a scalpel cut, the surgeon inserts a 10 mm to 11 mm cannula into the patients' body, by use of a surgical trocar. The staple carrying cartridge 70 and stapler 10 of the present invention are inserted through the cannula with the anvil 60 in closed position. Then, the anvil 60 is opened by return spring 66 after insertion into the body. Tissue may be manipulated into the jaws of the device 10 by using a tissue gripping mechanism inserted into the body through an alternate cannula. The surgeon closes the jaws 60, 70 by squeezing on the trigger 25 on the actuation mechanism 20. In this way, either the cam surfaces 82 force the anvil 60 onto the tissue, or a collar 90 is caused to enclose both the tissue carrying cartridge 70 and the anvil 60. During this activity a retaining pin 95 not shown, can be placed onto the tissue at the distal end of the anvil 60 to reinforce the alternate jaws 60, 70 used in stapling and clinching staples.

In subsequent steps, the surgeon activates lever 22 so that it fires the staples 51, and using knife 55, cuts between the center two rows of staples so that stapling and cutting is completed. Thereafter, the tissue can be removed by opening the anvil 60 away from the staple carrying cartridge 70. Once tissue is removed the anvil 60 can be closed on cartridge 70 so that it again fits within the cannula. After removing and disposing of the stapler 10, the trocar tube or cannula can be removed from the body. The opening in the body is then sutured or stapled closed.

It has been seen that the present invention describes a useful instrument for performing four row laparoscopic surgeries. In this way, tissue trauma is greatly reduced, and the person on whom surgery is being performed is capable of recuperating in adequate time. This invention is promising for those in the surgical stapling arena who will find it more useful in performing relatively mundane surgical stapling procedures with a new method of operation. It is therefore important to recognize that the invention is embodied in the attached claims and their equivalents.

What is claimed is:

1. A remotely operated surgical stapler configured to fit within a hollow cannula, comprising:
   a tubular sheath having two open ends;
   an actuating mechanism positioned at one end of said sheath;
   a stapling mechanism positioned at the opposite end of said sheath, said actuating mechanism capable of remotely actuating said stapling mechanism, and said stapling mechanism including a firing mechanism for firing staples, said firing mechanism connected to said actuating mechanism, and said stapling mechanism further, including an anvil mechanism for clinching said staples, and wherein said firing mechanism and said anvil mechanism are relatively pivotable about one another; and
   closure means for brining said firing mechanism and said anvil mechanism in close proximity to one another, said closure means comprising a cam remotely connected to said actuating mechanism and a cam follower attached to one of said anvil mechanism and said first mechanism, and wherein said cam follower is engageable with said cam such that said cam is capable of causing said cam follower to effect said relative pivoting motion of said anvil mechanism and said firing mechanism in order to bring said anvil mechanism and said firing mechanism into close proximity such that said staples may be fired; and
   wherein said closure means is located within the open tubular end of said sheath where said stapling mechanism is contained, such that said sheath does not contact said closure means.

2. The stapler of claim 1 wherein said sheath is slidable and when said anvil mechanism and firing mechanism are in close proximity, said sheath is positioned around said anvil and said firing mechanisms.

3. The stapler of claim 1 wherein said actuating mechanism is connected to a lever, said lever contacting said anvil and said firing mechanisms, said lever pivoting about said anvil mechanism to bring said firing mechanism in close proximity therewith.

4. The surgical stapler of claim 1 wherein said sheath fits within a cannula of about 11 mm diameter.

5. The surgical stapler of claim 1 wherein said firing mechanism is a ramp, said ramp attached to said actuating mechanism, said ramp interacting with drivers for driving staples such that when said ramp contacts said drivers, said staples are expelled from said firing mechanism toward said anvil mechanism.

6. The stapler of claim 1 further including knife means attached to said actuating means and operated between said firing mechanism and said anvil mechanism.

7. The stapler of claim 1 wherein said cam follower is located on said anvil mechanism, and said firing mechanism is stationary.

8. The stapler of claim 1 wherein said cam follower is located on said firing mechanism, and said anvil mechanism is stationary.

9. A surgical stapler comprising an anvil mechanism and a firing mechanism, said anvil mechanism pivotable relative to said firing mechanism, said firing mechanism attached to an actuating means, and closure means for pivoting said anvil and firing mechanisms into close proximity of one another, said closure means comprising a cam remotely connected to said actuating mechanism and a cam follower attached to one of said anvil mechanism and said firing mechanism, and wherein said cam follower is engageable with said cam such that said cam is capable of causing said cam follower to effect said relative pivoting motion of said anvil mechanism and said firing mechanism in order to bring said anvil mechanism and said firing mechanism into close proximity, such that said staples may be fired, and wherein said stapler contains a tubular sheath, a portion of which is slidable over said anvil mechanism and said firing mechanism during firing of said stapler, and said cam and cam follower held within said sheath.

10. The stapler of claim 9 wherein said cam follower is located on said anvil mechanism, and said firing mechanism is stationary.

11. The stapler of claim 9 wherein said cam follower is located on said firing mechanism, and said anvil mechanism is stationary.

12. The surgical stapler of claim 9 wherein said sheath fits within a cannula of about 11 mm diameter.

13. The surgical stapler of claim 9 wherein said firing mechanism is a ramp, said ramp attached to an actuating mechanism, said ramp interacting with drivers for driving staples such that when said ramp contacts said drivers, said staples are expelled from said firing mechanism toward said anvil mechanism.

14. The stapler of claim 9 further including knife means attached to an actuating means and operated between said firing mechanism and said anvil mechanism.

* * * * *